United States Patent
Mark et al.

(10) Patent No.: US 11,203,005 B2
(45) Date of Patent: Dec. 21, 2021

(54) METHOD FOR PRODUCING WATER-ABSORBING POLYMER PARTICLES BY SUSPENSION POLYMERIZATION

(71) Applicant: BASF SE, Ludwigshafen (DE)

(72) Inventors: Tina Mark, Hassloch (DE); Thomas Daniel, Waldsee (DE); Erich Lutz, Altrip (DE); Stefan Molter, Maxdorf (DE); Anna Kowalski, Frankenthal (DE)

(73) Assignee: BASF SE, Ludwigshafen (DE)

( * ) Notice: Subject to any disclaimer, the term of this patent is extended or adjusted under 35 U.S.C. 154(b) by 1034 days.

(21) Appl. No.: 15/532,153

(22) PCT Filed: Nov. 24, 2015

(86) PCT No.: PCT/EP2015/077431
§ 371 (c)(1),
(2) Date: Jun. 1, 2017

(87) PCT Pub. No.: WO2016/087262
PCT Pub. Date: Jun. 9, 2016

(65) Prior Publication Data
US 2017/0266640 A1    Sep. 21, 2017

(30) Foreign Application Priority Data

Dec. 4, 2014 (EP) .................... 14196175

(51) Int. Cl.
| | |
|---|---|
| C08F 2/18 | (2006.01) |
| B01J 20/26 | (2006.01) |
| A61L 15/60 | (2006.01) |
| C08J 3/24 | (2006.01) |
| A61F 13/53 | (2006.01) |
| A61L 15/24 | (2006.01) |
| B01J 20/30 | (2006.01) |
| C08F 20/06 | (2006.01) |

(52) U.S. Cl.
CPC ............ B01J 20/265 (2013.01); A61F 13/53 (2013.01); A61L 15/24 (2013.01); A61L 15/60 (2013.01); B01J 20/3085 (2013.01); C08F 2/18 (2013.01); C08F 20/06 (2013.01); C08J 3/245 (2013.01); A61F 2013/530226 (2013.01); C08J 2333/02 (2013.01)

(58) Field of Classification Search
CPC ........ B01J 20/265; B01J 20/3085; C08F 2/18; C08F 20/06; C08F 220/06; A61L 15/24; A61L 15/60; A61F 13/53; A61F 2013/530226; C08J 3/245; C08J 2333/02
See application file for complete search history.

(56) References Cited

U.S. PATENT DOCUMENTS

| | | | |
|---|---|---|---|
| 5,652,309 A | 7/1997 | Itoh et al. | |
| 6,060,557 A * | 5/2000 | Dahmen | A61L 15/60 174/110 V |
| 6,187,872 B1 * | 2/2001 | Yanase | A61L 15/60 525/330.2 |
| 8,084,556 B2 | 12/2011 | Funk | |
| 2007/0066167 A1 * | 3/2007 | Wada | C08J 3/12 442/101 |
| 2008/0125533 A1 * | 5/2008 | Riegel | A61L 15/60 524/417 |
| 2009/0036855 A1 * | 2/2009 | Wada | C08F 6/18 604/372 |
| 2009/0258994 A1 | 10/2009 | Even et al. | |
| 2011/0059329 A1 | 3/2011 | Dobrawa et al. | |
| 2011/0130735 A1 | 6/2011 | Weismantel et al. | |
| 2011/0238026 A1 * | 9/2011 | Zhang | A61F 13/534 604/372 |
| 2016/0280825 A1 | 9/2016 | Bauer et al. | |

FOREIGN PATENT DOCUMENTS

| | | |
|---|---|---|
| CN | 1146997 A | 4/1997 |
| CN | 101558083 A | 10/2009 |
| EP | 1 433 526 A2 | 6/2004 |
| JP | S63218702 A | 9/1988 |
| WO | WO-2006/014031 A1 | 2/2006 |
| WO | WO-2008/026783 A1 | 3/2008 |
| WO | WO-2008/068208 A1 | 6/2008 |
| WO | WO-2015/062883 A2 | 5/2015 |
| WO | WO-2015/110321 A1 | 7/2015 |

OTHER PUBLICATIONS

Buchholz, Fredric L., et al., "Commercial Processes for the Manufacture of Superabsorbent Polymers," *Modern Superabsorbent Polymer Technology*, New York: John Wiley & Sons, Inc., 1998, pp. 69-117.

International Search Report and Written Opinion for PCT Patent Application No. PCT/EP2015/077431, dated Feb. 16, 2016 (12 pages).

* cited by examiner

*Primary Examiner* — Robert C Boyle
(74) *Attorney, Agent, or Firm* — Marshall, Gerstein & Borun LLP

(57) ABSTRACT

A process for producing water-absorbing polymer particles by suspension polymerization and thermal surface postcrosslinking, wherein the agglomerated base polymer obtained by suspension polymerization has a centrifuge retention capacity of at least 37 g/g and the thermal surface postcrosslinking is conducted at 100 to 190° C.

11 Claims, No Drawings

METHOD FOR PRODUCING WATER-ABSORBING POLYMER PARTICLES BY SUSPENSION POLYMERIZATION

CROSS-REFERENCED TO RELATED APPLICATIONS

This application is the U.S. National Stage application of International Patent Application No. PCT/EP2015/077431, filed Nov. 24, 2015, which claims the benefit of European Patent Application No. 14196175.5, filed Dec. 4, 2014.

The present invention relates to a process for producing water-absorbing polymer particles by suspension polymerization and thermal surface postcrosslinking, wherein the agglomerated base polymer obtained by suspension polymerization has a centrifuge retention capacity of at least 37 g/g and the thermal surface postcrosslinking is conducted at 100 to 190° C.

The production of water-absorbing polymer particles is described in the monograph "Modern Superabsorbent Polymer Technology", F. L. Buchholz and A. T. Graham, Wiley-VCH, 1998, pages 69 to 117. The water-absorbing polymer particles are typically produced by solution polymerization or suspension polymerization.

Being products which absorb aqueous solutions, water-absorbing polymers are used to produce diapers, tampons, sanitary napkins and other hygiene articles, but also as water-retaining agents in market gardening.

The properties of the water-absorbing polymers can be adjusted via the level of crosslinking. With increasing level of crosslinking, there is a rise in gel strength and a fall in absorption capacity.

To improve the use properties, for example permeability in the swollen gel bed in the diaper and absorption under pressure, water-absorbing polymer particles are generally surface postcrosslinked. This increases only the level of crosslinking of the particle surface, and in this way it is possible to at least partly decouple absorption under pressure and centrifuge retention capacity.

JP S63-218702 describes a continuous process for producing water-absorbing polymer particles by suspension polymerization.

WO 2006/014031 A1 describes a process for producing water-absorbing polymer particles by suspension polymerization. At the high temperatures in the thermal postcrosslinking, the fraction of hydrophobic solvent is driven out.

WO 2008/068208 A1 likewise relates to a process for producing water-absorbing polymer particles having a low proportion of hydrophobic solvents by suspension polymerization.

It was an object of the present invention to provide an improved process for producing water-absorbing polymer particles by suspension polymerization, wherein the water-absorbing polymer particles should have a high centrifuge retention capacity (CRC), a high absorption under a pressure of 49.2 g/cm² (AUHL), a high sum total of centrifuge retention capacity (CRC) and absorption under a pressure of 49.2 g/cm² (AUHL), and a low level of extractables.

The object was achieved by a process for producing water-absorbing polymer particles by polymerizing a monomer solution comprising a) at least one ethylenically unsaturated monomer which bears acid groups and may have been at least partly neutralized,
b) optionally one or more crosslinkers,
c) at least one initiator,
d) optionally one or more ethylenically unsaturated monomers copolymerizable with the monomers mentioned under a) and
e) optionally one or more water-soluble polymers, the monomer solution suspended in a hydrophobic organic solvent during the polymerization being agglomerated during or after the polymerization in the hydrophobic organic solvent, and thermally surface postcrosslinking the resultant agglomerated polymer particles by means of an organic surface postcrosslinker, wherein the amount of crosslinker b) is selected such that the agglomerated polymer particles before the surface postcrosslinking have a centrifuge retention capacity of at least 37 g/g and the thermal surface postcrosslinking is conducted at 100 to 190° C.

In a preferred embodiment of the present invention, the amount of crosslinker b) is selected such that the agglomerated polymer particles, prior to the surface postcrosslinking, have a centrifuge retention capacity of at least 38 g/g, and the thermal surface postcrosslinking is conducted at 105 to 180° C.

In a particularly preferred embodiment of the present invention, the amount of crosslinker b) is selected such that the agglomerated polymer particles, prior to the surface postcrosslinking, have a centrifuge retention capacity of at least 39 g/g, and the thermal surface postcrosslinking is conducted at 110 to 175° C.

In a very particularly preferred embodiment of the present invention, the amount of crosslinker b) is selected such that the agglomerated polymer particles, prior to the surface postcrosslinking, have a centrifuge retention capacity of at least 40 g/g, and the thermal surface postcrosslinking is conducted at 120 to 170° C.

The monomers a) are preferably water-soluble, i.e. the solubility in water at 23° C. is typically at least 1 g/100 g of water, preferably at least 5 g/100 g of water, more preferably at least 25 g/100 g of water and most preferably at least 35 g/100 g of water.

Suitable monomers a) are, for example, ethylenically unsaturated carboxylic acids, such as acrylic acid, methacrylic acid and itaconic acid. Particularly preferred monomers are acrylic acid and methacrylic acid. Very particular preference is given to acrylic acid.

Further suitable monomers a) are, for example, ethylenically unsaturated sulfonic acids, such as styrenesulfonic acid and 2-acrylamido-2-methylpropanesulfonic acid (AMPS).

Impurities can have a considerable influence on the polymerization. The raw materials used should therefore have a maximum purity. It is therefore often advantageous to specially purify the monomers a). Suitable purification processes are described, for example, in WO 2002/055469 A1, WO 2003/078378 A1 and WO 2004/035514 A1. A suitable monomer a) is, for example, an acrylic acid purified according to WO 2004/035514 A1 and comprising 99.8460% by weight of acrylic acid, 0.0950% by weight of acetic acid, 0.0332% by weight of water, 0.0203% by weight of propionic acid, 0.0001% by weight of furfurals, 0.0001% by weight of maleic anhydride, 0.0003% by weight of diacrylic acid and 0.0050% by weight of hydroquinone monomethyl ether.

The proportion of acrylic acid and/or salts thereof in the total amount of monomers a) is preferably at least 50 mol %, more preferably at least 90 mol %, most preferably at least 95 mol %.

The acid groups of the monomers a) may have been partly neutralized. The neutralization is conducted at the monomer stage. This is typically accomplished by mixing in the neutralizing agent as an aqueous solution or else preferably as a solid. The degree of neutralization is preferably from 25 to 95 mol %, more preferably from 30 to 80 mol % and most preferably from 40 to 75 mol %, for which the customary neutralizing agents can be used, preferably alkali metal hydroxides, alkali metal oxides, alkali metal carbonates or alkali metal hydrogencarbonates and also mixtures thereof. Instead of alkali metal salts, it is also possible to use ammonium salts.

Particularly preferred alkali metals are sodium and potassium, but very particular preference is given to sodium hydroxide, sodium carbonate or sodium hydrogencarbonate and also mixtures thereof.

The monomers a) typically comprise polymerization inhibitors, preferably hydroquinone monoethers, as storage stabilizers.

The monomer solution comprises preferably up to 250 ppm by weight, preferably at most 130 ppm by weight, more preferably at most 70 ppm by weight, and preferably at least 10 ppm by weight, more preferably at least 30 ppm by weight and especially around 50 ppm by weight, of hydroquinone monoether, based in each case on the unneutralized monomer a). For example, the monomer solution can be prepared by using an ethylenically unsaturated monomer bearing acid groups with an appropriate content of hydroquinone monoether.

Preferred hydroquinone monoethers are hydroquinone monomethyl ether (MEHQ) and/or alpha-tocopherol (vitamin E). Suitable crosslinkers b) are compounds having at least two groups suitable for crosslinking. Such groups are, for example, ethylenically unsaturated groups which can be polymerized free-radically into the polymer chain, and functional groups which can form covalent bonds with the acid groups of the monomer a). In addition, polyvalent metal salts which can form coordinate bonds with at least two acid groups of the monomer a) are also suitable as crosslinkers b).

Crosslinkers b) are preferably compounds having at least two polymerizable groups which can be polymerized free-radically into the polymer network. Suitable crosslinkers b) are, for example, methylenebisacrylamide, ethylene glycol dimethacrylate, diethylene glycol diacrylate, polyethylene glycol diacrylate, allyl methacrylate, trimethylolpropane triacrylate, triallylamine, tetraallylammonium chloride, tetraallyloxyethane, as described in EP 0 530 438 A1, di- and triacrylates, as described in EP 0 547 847 A1, EP 0 559 476 A1, EP 0 632 068 A1, WO 93/21237 A1, WO 2003/104299 A1, WO 2003/104300 A1, WO 2003/104301 A1 and DE 103 31 450 A1, mixed acrylates which, as well as acrylate groups, comprise further ethylenically unsaturated groups, as described in DE 103 31 456 A1 and DE 103 55 401 A1, or crosslinker mixtures, as described, for example, in DE 195 43 368 A1, DE 196 46 484 A1, WO 90/15830 A1 and WO 2002/032962 A2.

Preferred crosslinkers b) are pentaerythrityl triallyl ether, tetraallyloxyethane, methylenebismethacrylamide, 15-tuply ethoxylated trimethylolpropane triacrylate, polyethylene glycol diacrylate, trimethylolpropane triacrylate and triallylamine.

Very particularly preferred crosslinkers b) are methylenebisacrylamide and the polyethoxylated and/or -propoxylated glycerols which have been esterified with acrylic acid or methacrylic acid to give di- or triacrylates, as described, for example, in WO 2003/104301 A1.

Methylenebisacrylamide and di- and/or triacrylates of 3- to 10-tuply ethoxylated glycerol are particularly advantageous. Very particular preference is given to methylenebisacrylamide, di- or triacrylates of 1- to 5-tuply ethoxylated and/or propoxylated glycerol. Most preferred are methylenebisacrylamide and the triacrylates of 3- to 5-tuply ethoxylated and/or propoxylated glycerol, especially methylenebisacrylamide and the triacrylate of 3-tuply ethoxylated glycerol.

The amount of crosslinker in the monomer solution is selected such that the water-absorbing polymer particles after the polymerization and before the thermal surface postcrosslinking (base polymer) have a centrifuge retention capacity (CRC) of at least 37 g/g, preferably at least 38 g/g, more preferably at least 39 g/g, most preferably at least 40 g/g. The centrifuge retention capacity (CRC) should not exceed 75 g/g. If the centrifuge retention capacity (CRC) of the base polymer is too high, it is not possible to build up sufficient absorption under a pressure of 49.2 g/cm$^2$ (AUHL) in the subsequent thermal surface postcrosslinking.

Initiators c) used may be all compounds which generate free radicals under the polymerization conditions, for example thermal initiators, redox initiators or photoinitiators. Suitable redox initiators are potassium peroxodisulfate or sodium peroxodisulfate/ascorbic acid, hydrogen peroxide/ascorbic acid, potassium peroxodisulfate or sodium peroxodisulfate/sodium bisulfite and hydrogen peroxide/sodium bisulfite. Preference is given to using mixtures of thermal initiators and redox initiators, such as potassium peroxodisulfate or sodium peroxodisulfate/hydrogen peroxide/ascorbic acid. The reducing component used is, however, preferably a mixture of the sodium salt of 2-hydroxy-2-sulfinatoacetic acid, the disodium salt of 2-hydroxy-2-sulfonatoacetic acid and sodium bisulfite. Such mixtures are obtainable as Brüggolite® FF6 and Brüggolite® FF7 (Bruggemann Chemicals; Heilbronn; Germany).

Suitable thermal initiators are especially azo initiators, such as 2,2'-azobis[2-(2-imidazolin-2-yl)propane] dihydrochloride and 2,2'-azobis[2-(5-methyl-2-imidazolin-2-yl)propane] dihydrochloride, 2,2"-azobis(2-amidinopropane) dihydrochloride, 4,4"-azobis(4-cyanopentanoic acid), 4,4' and the sodium salts thereof, 2,2"-azobis[2-methyl-N-(2-hydroxyethyl)propionamide] and 2,2'-azobis(imino-1-pyrrolidino-2-ethylpropane) dihydrochloride.

Suitable photoinitiators are, for example, 2-hydroxy-2-methylpropiophenone and 1-[4-(2-hydroxyethoxy)phenyl]-2-hydroxy-2-methyl-1-propan-1-one.

Ethylenically unsaturated monomers d) copolymerizable with the ethylenically unsaturated monomers a) bearing acid groups are, for example, acrylamide, methacrylamide, hydroxyethyl acrylate, hydroxyethyl methacrylate, dimethylaminoethyl methacrylate, dimethylaminoethyl acrylate, dimethylaminopropyl acrylate, diethylaminopropyl acrylate, dimethylaminoethyl methacrylate, diethylaminoethyl methacrylate.

The water-soluble polymers e) used may be polyvinyl alcohol, polyvinylpyrrolidone, starch, starch derivatives, modified cellulose, such as methyl cellulose or hydroxyethyl cellulose, gelatin, polyglycols or polyacrylic acids, preferably starch, starch derivatives and modified cellulose.

Optionally, one or more chelating agents may be added to the monomer solution or starting materials thereof to mask metal ions, for example iron, for the purpose of stabilization. Suitable chelating agents are, for example, alkali metal citrates, citric acid, alkali metal tartrates, pentasodium triphosphate, ethylenediamine tetraacetate, nitrilotriacetic acid, and also all chelating agents known by the Trilon® name, for example Trilon® C (pentasodium diethylenetriaminepentaacetate), Trilon® D (trisodium (hydroxyethyl) ethylenediaminetriacetate), and Trilon® M (methylglycinediacetic acid).

For optimal action, the preferred polymerization inhibitors require dissolved oxygen. The monomer solution can therefore be freed of dissolved oxygen before the polymerization by inertization, i.e. flowing an inert gas through, preferably nitrogen or carbon dioxide. If the polymerization is conducted under adequate reflux, the inertization can be dispensed with. In this case, the dissolved oxygen is removed from the polymerization reactor together with the evaporating solvent.

For polymerization, the monomer solution is suspended or emulsified in a hydrophobic solvent.

Usable hydrophobic solvents are all the solvents known to the person skilled in the art for use in suspension polymerization. Preference is given to using aliphatic hydrocarbons, such as n-hexane, n-heptane, n-octane, n-nonane, n-decane, cyclohexane or mixtures thereof. Hydrophobic solvents have a solubility in water at 23° C. of less than 5 g/100 g, preferably less than 1 g/100 g, more preferably less than 0.5 g/100 g.

The hydrophobic solvent boils within the range from preferably 50 to 150° C., more preferably 60 to 120° C., most preferably 70 to 90° C.

The ratio between hydrophobic solvent and monomer solution is 0.2 to 3.0, preferably 0.3 to 2.7 and very preferably from 0.4 to 2.4.

For dispersion of the aqueous monomer solution in the hydrophobic solvent or for dispersion of the water-absorbing polymer particles which form, it is possible to add dispersing aids. These dispersing aids may be anionic, cationic, nonionic or amphoteric surfactants, or natural, semisynthetic or synthetic polymers.

Anionic surfactants are, for example, sodium polyoxyethylene dodecyl ether sulfate and sodium dodecyl ether sulfate. A cationic surfactant is, for example, trimethylstearylammonium chloride. An amphoteric surfactant is, for example, carboxymethyldimethylcetylammonium. Nonionic surfactants are, for example, sucrose fatty acid esters, such as sucrose monostearate and sucrose dilaurate, sorbitan esters such as sorbitan monostearate, trehalose fatty acid esters, such as trehalose stearate, polyoxyalkylene compounds based on sorbitan esters, such as polyoxyethylenesorbitan monostearate.

Suitable polymers are, for example, cellulose derivatives such as hydroxyethyl cellulose, methyl hydroxyethyl cellulose, methyl hydroxypropyl cellulose, methyl cellulose and carboxymethyl cellulose, polyvinylpyrrolidone, copolymers of vinylpyrrolidone, gelatin, gum arabic, xanthan, casein, polyglycerols, polyglycerol fatty acid esters, polyethylene glycols, modified polyethylene glycol such as polyethylene glycol stearate or polyethylene glycol stearyl ether stearate, polyvinyl alcohol, partially hydrolyzed polyvinyl acetates and modified polyethylene, such as a maleic acid-modified polyethylene.

It is also possible to use inorganic particles as dispersing aids, these being called Pickering systems. Such a Pickering system may consist of the solid particles on their own or additionally of auxiliaries which improve the dispersibility of the particles in water or the wettability of the particles by the hydrophobic solvent. The way in which they work and their use are described in WO 99/24525 A1 and EP 1 321 182 A1.

The inorganic solid particles may be metal salts, such as salts, oxides and hydroxides of calcium, magnesium, iron, zinc, nickel, titanium, aluminum, silicon, barium and manganese. These include magnesium hydroxide, magnesium carbonate, magnesium oxide, calcium oxalate, calcium carbonate, barium carbonate, barium sulfate, titanium dioxide, aluminum oxide, aluminum hydroxide and zinc sulfide. These likewise include silicates, bentonite, hydroxyapatite and hydrotalcites. Particular preference is given to $SiO_2$-based silicas, magnesium pyrophosphate and tricalcium phosphate.

Suitable $SiO_2$-based dispersing aids are finely divided silicas. These can be dispersed in water as fine solid particles. It is also possible to use what are called colloidal dispersions of silica in water. Such colloidal dispersions are alkaline aqueous mixtures of silica. In the alkaline pH range, the particles are swollen and stable in water. Preferred colloidal dispersions of silica, at pH 9.3, have a specific surface area in the range from 20 to 90 $m^2/g$.

In addition, it is possible to use any desired mixtures of the dispersing aids.

The dispersing aid is typically dissolved or dispersed in the hydrophobic solvent. The dispersing aid is used in amounts between 0.01 and 10% by weight, preferably between 0.2 and 5% by weight, more preferably between 0.5 and 2% by weight, based on the monomer solution. The diameter of the monomer solution droplets can be adjusted via the type and amount of dispersing aid.

The diameter of the monomer solution droplets can be adjusted via the stirrer energy introduced and through suitable dispersing aids.

The performance of the agglomeration is known to those skilled in the art and is not subject to any restrictions. The polymerization and the agglomeration can be conducted simultaneously (one-stage metering) or successively (two-stage metering).

In the case of one-stage metering, the monomer solution is metered into the hydrophobic solvent and the droplets of monomer solution agglomerate during the polymerization.

In the case of two-stage metering, a first monomer solution is first metered into the hydrophobic solvent and the droplets of monomer solution are polymerized. Then a second monomer solution is metered into the dispersed polymer particles thus obtained and polymerization is effected again. The polymer particles do not agglomerate until the second polymerization. The first and second monomer solutions may be identical or different in terms of composition.

With every further addition of monomer to agglomerates that have already formed, irrespective of whether they have been prepared by one-stage or two-stage metering, the agglomerates can be agglomerated further to give larger agglomerates.

There may be cooling steps between the metered additions of monomer. Some of the dispersing aid may precipitate out therein.

Whether the droplets of the monomer solution agglomerate or not during the polymerization can be established via the type and amount of the dispersing aid. Given a sufficient amount of dispersing aid, agglomeration during the polymerization of the droplets of monomer solution is prevented. The amount necessary for this purpose depends on the type of dispersing aid.

Preference is given to two-stage metered addition, i.e. agglomeration after the polymerization of the droplets of monomer solution.

Advantageously, several stirred reactors are connected in series for the polymerization. Through postreaction in further stirred reactors, the monomer conversion can be increased and backmixing can be reduced. In this context, it is additionally advantageous when the first stirred reactor is not too large. With increasing size of the stirred reactor, there is inevitably broadening of the size distribution of the dispersed monomer solution droplets. A relatively small first reactor therefore enables the production of water-absorbing polymer particles with a particularly narrow particle size distribution.

The reaction is preferably conducted under reduced pressure, for example at a pressure of 800 mbar. The pressure can be used to set the boiling point of the reaction mixture to the desired reaction temperature.

In a preferred embodiment of the present invention, the polymerization is conducted in the presence of a typically water-soluble chain transfer reagent.

Chain transfer reagents intervene in the polymerization kinetics and control the molar mass. Suitable chain transfer reagents are thiols, thiol acids, secondary alcohols, phosphorus compounds, lactic acid, aminocarboxylic acids, etc.

The chain transfer reagent is used in an amount of preferably 0.00001 to 0.1 mol/mol, more preferably of 0.00015 to 0.08 mol/mol, most preferably 0.0002 to 0.06 mol/mol, based in each case on the monomer a).

The resultant water-absorbing polymer particles are thermally surface postcrosslinked. The thermal surface postcrosslinking can be conducted in the polymer dispersion or with the water-absorbing polymer particles which have been removed from the polymer dispersion and dried.

Addition of the monomer solution may also be above the boiling point of water or of the solvent or the solvent/water azeotrope, such that solvent or a solvent/water azeotrope is distilled off continuously during the addition of monomer.

In a preferred embodiment of the present invention, the water-absorbing polymer particles are dewatered azeotropically in the polymer dispersion and filtered out of the polymer dispersion, and the filtered water-absorbing polymer particles are dried to remove the adhering residual hydrophobic solvent and thermally surface postcrosslinked.

Suitable surface postcrosslinkers are compounds which comprise groups which can form covalent bonds with at least two carboxylate groups of the polymer particles. Suitable compounds are, for example, polyfunctional amines, polyfunctional amido amines, polyfunctional epoxides, as described in EP 0 083 022 A2, EP 0 543 303 A1 and EP 0 937 736 A2, di- or polyfunctional alcohols, as described in DE 33 14 019 A1, DE 35 23 617 A1 and EP 0 450 922 A2, or β-hydroxyalkylamides, as described in DE 102 04 938 A1 and U.S. Pat. No. 6,239,230.

Additionally described as suitable surface postcrosslinkers are alkylene carbonates in DE 40 20 780 C1, 2-oxazolidinone and derivatives thereof, such as 2-hydroxyethyl-2-oxazolidinone, in DE 198 07 502 A1, bis- and poly-2-oxazolidinones in DE 198 07 992 C1, 2-oxotetrahydro-1,3-oxazine and derivatives thereof in DE 198 54 573 A1, N-acyl-2-oxazolidinones in DE 198 54 574 A1, cyclic ureas in DE 102 04 937 A1, bicyclic amido acetals in DE 103 34 584 A1, oxetanes and cyclic ureas in EP 1 199 327 A2 and morpholine-2,3-dione and derivatives thereof in WO 2003/031482 A1.

In addition, it is also possible to use surface postcrosslinkers which comprise additional polymerizable ethylenically unsaturated groups, as described in DE 37 13 601 A1.

In addition, it is possible to use any desired mixtures of the suitable surface postcrosslinkers.

Preferred surface postcrosslinkers are alkylene carbonates, 2-oxazolidinones, bis- and poly-2-oxazolidinones, 2-oxotetrahydro-1,3-oxazines, N-acyl-2-oxazolidinones, cyclic ureas, bicyclic amido acetals, oxetanes, bisoxetanes and morpholine-2,3-diones.

Particularly preferred surface postcrosslinkers are ethylene carbonate (1,3-dioxolan-2-one), trimethylene carbonate (1,3-dioxan-2-one), 3-methyl-3-oxethanemethanol, 2-hydroxyethyl-2-oxazolidinone, 2-oxazolidinone and methyl-2-oxazolidinone.

Very particular preference is given to ethylene carbonate.

The amount of surface postcrosslinker is preferably 0.1% to 10% by weight, more preferably 0.5% to 7.5% by weight and most preferably 1% to 5% by weight, based in each case on the polymer particles.

The surface postcrosslinkers are typically used in the form of an aqueous solution. The amount of the solvent is preferably 0.001 to 8% by weight, more preferably 2 to 7% by weight, even more preferably 3 to 6% by weight and especially 4 to 5% by weight, based in each case on the polymer particles. The penetration depth of the surface postcrosslinker into the polymer particles can be adjusted via the content of nonaqueous solvent and total amount of solvent.

When exclusively water is used as the solvent, a surfactant is advantageously added. This improves the wetting characteristics and reduces the tendency to form lumps. However, preference is given to using solvent mixtures, for example isopropanol/water, 1,3-propanediol/water and propylene glycol/water, where the mixing ratio in terms of mass is preferably from 10:90 to 60:40.

In a preferred embodiment of the present invention, cations, especially polyvalent cations, are applied to the particle surface in addition to the surface postcrosslinkers before, during or after the thermal surface postcrosslinking.

The polyvalent cations usable in the process according to the invention are, for example, divalent cations such as the cations of zinc, magnesium, calcium, iron and strontium, trivalent cations such as the cations of aluminum, iron, chromium, rare earths and manganese, tetravalent cations such as the cations of titanium and zirconium. Possible counterions are hydroxide, chloride, bromide, sulfate, hydrogensulfate, carbonate, hydrogencarbonate, nitrate, phosphate, hydrogenphosphate, dihydrogenphosphate and carboxylate, such as acetate, citrate and lactate. Salts with different counterions are also possible, for example basic aluminum salts such as aluminum monoacetate or aluminum monolactate. Aluminum sulfate, aluminum monoacetate and aluminum lactate are preferred. Apart from metal salts, it is also possible to use polyamines as polyvalent cations.

The amount of polyvalent cation used is, for example, 0.001% to 1.5% by weight, preferably 0.005% to 1% by weight and more preferably 0.02% to 0.8% by weight, based in each case on the polymer particles.

In a further preferred embodiment of the present invention, hydrophilizing agents are additionally applied before, during or after the thermal surface postcrosslinking, for example sugar alcohols such as sorbitol, mannitol and xylitol, water-soluble polymers or copolymers such as cellulose, polyethylene glycols, polyvinyl alcohols, polyvinylpyrrolidones and polyacrylamides.

The surface postcrosslinking is typically performed in such a way that a solution of the surface postcrosslinker is sprayed onto the dried polymer particles. After the spray application, the surface postcrosslinker-coated polymer particles are thermally surface postcrosslinked.

The spray application of a solution of the surface postcrosslinker is preferably performed in mixers with moving mixing tools, such as screw mixers, disk mixers and paddle mixers. Particular preference is given to horizontal mixers such as paddle mixers, very particular preference to vertical mixers. The distinction between horizontal mixers and vertical mixers is made by the position of the mixing shaft, i.e. horizontal mixers have a horizontally mounted mixing shaft and vertical mixers a vertically mounted mixing shaft. Suitable mixers are, for example, horizontal Pflugschar® plowshare mixers (Gebr. Lödige Maschinenbau GmbH; Paderborn; Germany), Vrieco-Nauta continuous mixers (Hosokawa Micron BV; Doetinchem; the Netherlands), Processall Mixmill mixers (Processall Incorporated; Cincinnati; USA) and Schugi Flexomix® (Hosokawa Micron BV; Doetinchem; the Netherlands). However, it is also possible to spray on the surface postcrosslinker solution in a fluidized bed.

The thermal surface postcrosslinking is preferably performed in contact driers, more preferably paddle driers, most preferably disk driers. Suitable driers are, for example, Hosokawa Bepex® Horizontal Paddle Dryers (Hosokawa Micron GmbH; Leingarten; Germany), Hosokawa Bepex® Disc Dryers (Hosokawa Micron GmbH; Leingarten; Germany), Holo-Flite® driers (Metso Minerals Industries Inc.; Danville; USA) and Nara Paddle Dryers (NARA Machinery Europe; Frechen; Germany). Moreover, fluidized bed driers may also be used.

The thermal surface postcrosslinking can be effected in the mixer itself, by heating the jacket or blowing in warm air. Equally suitable is a downstream drier, for example a shelf drier, a rotary tube oven or a heatable screw. It is particularly advantageous to effect mixing and thermal surface postcrosslinking in a fluidized bed drier.

It may be advantageous to conduct the thermal surface postcrosslinking under reduced pressure or to conduct it with use of drying gases, for example dried air and nitrogen, in order to ensure the very substantial removal of the solvents.

Subsequently, the surface postcrosslinked polymer particles can be classified, with removal of excessively small and/or excessively large polymer particles and recycling thereof into the process.

The surface postcrosslinking can also be conducted in the polymer dispersion. For this purpose, the solution of the surface postcrosslinker is added to the polymer dispersion. In this context, it may be advantageous to conduct the thermal surface postcrosslinking under elevated pressure, for example with use of hydrophobic organic solvents having a boiling point at 1013 mbar below the desired temperature for the thermal surface postcrosslinking. After the thermal surface postcrosslinking in the polymer dispersion, the water-absorbing polymer particles are dewatered azeotropically in the polymer dispersion and removed from the polymer dispersion, and the water-absorbing polymer particles removed are dried to remove the adhering residual hydrophobic solvent.

Preferred surface postcrosslinking temperatures are in the range of 100 to 190° C., preferably in the range of 105 to 180° C., more preferably in the range of 110 to 175° C., most preferably in the range of 120 to 170° C. The preferred residence time at this temperature is preferably at least 10 minutes, more preferably at least 20 minutes, most preferably at least 30 minutes, and typically at most 120 minutes.

In a preferred embodiment of the present invention, the water-absorbing polymer particles are cooled after the thermal surface postcrosslinking in a contact drier. The cooling is preferably performed in contact coolers, more preferably paddle coolers and most preferably disk coolers. Suitable coolers are, for example, Hosokawa Bepex® Horizontal Paddle Cooler (Hosokawa Micron GmbH; Leingarten; Germany), Hosokawa Bepex® Disc Cooler (Hosokawa Micron GmbH; Leingarten; Germany), Holo-Flite® coolers (Metso Minerals Industries Inc.; Danville; USA) and Nara Paddle Cooler (NARA Machinery Europe; Frechen; Germany). Moreover, fluidized bed coolers may also be used.

In the cooler, the water-absorbing polymer particles are cooled to 20 to 150° C., preferably 30 to 120° C., more preferably 40 to 100° C. and most preferably 50 to 80° C.

To further improve the properties, the polymer particles thermally surface postcrosslinked in a contact drier can be coated or remoisturized.

The remoisturizing is preferably performed at 30 to 80° C., more preferably at 35 to 70° C., most preferably at 40 to 60° C. At excessively low temperatures, the water-absorbing polymer particles tend to form lumps, and, at higher temperatures, water already evaporates to a noticeable degree. The amount of water used for remoisturizing is preferably from 1 to 10% by weight, more preferably from 2 to 8% by weight and most preferably from 3 to 5% by weight. The remoisturizing increases the mechanical stability of the polymer particles and reduces their tendency to static charging.

Suitable coatings for improving the free swell rate and the permeability (SFC) are, for example, inorganic inert substances, such as water-insoluble metal salts, organic polymers, cationic polymers and di- or polyvalent metal cations. Suitable coatings for dust binding are, for example, polyols. Suitable coatings for counteracting the undesired caking tendency of the polymer particles are, for example, fumed silica, such as Aerosil® 200, and surfactants, such as Span® 20 and Plantacare 818 UP and surfactant mixtures.

The present invention further provides the water-absorbing polymer particles obtainable by the process according to the invention.

The water-absorbing polymer particles obtainable by the process according to the invention have a centrifuge retention capacity (CRC) of at least 37 g/g, an absorption under a pressure of 21.0 g/cm$^2$ of at least 30 g/g, an absorption under a pressure of 49.2 g/cm$^2$ (AUHL) of at least 14 g/g, a sum total of centrifuge retention capacity and absorption under a pressure of 21.0 g/cm$^2$ (CRC+AUL) of at least 69 g/g, a sum total of centrifuge retention capacity and absorption under a pressure of 49.2 g/cm$^2$ (CRC+AUHL) of at least 54 g/g, and less than 20% by weight of extractables.

The inventive water-absorbing polymer particles have a centrifuge retention capacity (CRC) of preferably at least 38 g/g, more preferably at least 40 g/g and most preferably at least 41 g/g. The centrifuge retention capacity (CRC) of the water-absorbing polymer particles is typically less than 75 g/g.

The inventive water-absorbing polymer particles have an absorption under a pressure of 21.0 g/cm$^2$ (AUL) of preferably at least 32 g/g, more preferably at least 33 g/g and most preferably at least 34 g/g. The absorption under a pressure of 21.0 g/cm$^2$ (AUL) of the water-absorbing polymer particles is typically less than 50 g/g.

The inventive water-absorbing polymer particles have an absorption under a pressure of 49.2 g/cm$^2$ (AUHL) of preferably at least 16 g/g, more preferably at least 18 g/g and most preferably at least 20 g/g. The absorption under a pressure of 49.2 g/cm$^2$ (AUHL) of the water-absorbing polymer particles is typically less than 35 g/g.

The sum total of centrifuge retention capacity (CRC) and absorption under a pressure of 21.0 g/cm$^2$ (AUL) of the inventive water-absorbing polymer particles is preferably at least 71 g/g, more preferably at least 73 g/g, most preferably at least 74 g/g.

The sum total of centrifuge retention capacity (CRC) and absorption under a pressure of 49.2 g/cm² (AUHL) of the inventive water-absorbing polymer particles is preferably at least 56 g/g, more preferably at least 58 g/g, most preferably at least 59 g/g.

The inventive water-absorbing polymer particles comprise preferably less than 17% by weight, more preferably less than 15% by weight and most preferably less than 14% by weight of extractables.

The inventive water-absorbing polymer particles have a proportion of particles having a particle size of 300 to 600 µm of preferably at least 30% by weight, more preferably at least 40% by weight and most preferably at least 50% by weight.

The present invention further provides hygiene articles comprising
(A) an upper liquid-permeable layer,
(B) a lower liquid-impermeable layer,
(C) a liquid-absorbing storage layer between layer (A) and layer (B), comprising from 0 to 30% by weight of a fibrous material and from 70 to 100% by weight of water-absorbing polymer particles obtainable by the process according to the invention,
(D) optionally an acquisition and distribution layer between layer (A) and layer (C), comprising from 80 to 100% by weight of a fibrous material and from 0 to 20% by weight of water-absorbing polymer particles obtainable by the process according to the invention,
(E) optionally a fabric layer directly above and/or beneath layer (C) and
(F) further optional components.

The proportion of water-absorbing polymer particles obtainable by the process according to the invention in the liquid-absorbing storage layer (C) is preferably at least 75% by weight, more preferably at least 80% by weight, most preferably at least 90% by weight.

The mean sphericity of the water-absorbing polymer particles obtainable by the process according to the invention in the liquid-absorbing storage layer (C) is preferably less than 0.84, more preferably less than 0.82, most preferably less than 0.80.

Water-absorbing polymer particles having relatively low sphericity are obtained by suspension polymerization when the polymer particles are agglomerated during or after the polymerization. In the inventive hygiene articles, agglomerated water-absorbing polymer particles are used.

The water-absorbing polymer particles are tested by means of the test methods described below.

Methods:

The measurements should, unless stated otherwise, be conducted at an ambient temperature of 23±2° C. and a relative air humidity of 50±10%. The water-absorbing polymers are mixed thoroughly before the measurement.

Residual Monomers

The residual monomer content of the water-absorbing polymer particles is determined by EDANA recommended test method WSP No. 210.2-05 "Residual Monomers".

Moisture Content

The moisture content of the water-absorbing polymer particles is determined by EDANA recommended test method No. WSP 230.3 (11) "Mass Loss Upon Heating".

Centrifuge Retention Capacity

The centrifuge retention capacity (CRC) is determined by EDANA recommended test method No. WSP 241.3(11) "Fluid Retention Capacity in Saline, After Centrifugation".

Absorption Under A Pressure of 0.0 g/cm²

The absorption under a pressure of 0.0 g/cm² (AUNL) is determined analogously to EDANA recommended test method No. WSP 242.3 (11) "Gravimetric Determination of Absorption Under Pressure", except that a pressure of 0.0 g/cm² (AUL0.0psi) is established instead of a pressure of 21.0 g/cm² (AUL0.3 psi).

Absorption Under A Pressure of 21.0 g/cm²

The absorption under a pressure of 21.0 g/cm² (AUL) of the water-absorbing polymer particles is determined by EDANA recommended test method No. WSP 242.3 (11) "Gravimetric Determination of Absorption Under Pressure".

Absorption Under A Pressure of 49.2 g/cm²

The absorption under a pressure of 49.2 g/cm² (AUHL) is determined analogously to EDANA recommended test method No. WSP 242.3 (11) "Gravimetric Determination of Absorption Under Pressure", except that a pressure of 49.2 g/cm² (AUL0.7 psi) is established instead of a pressure of 21.0 g/cm² (AUL0.3 psi).

Bulk Density

The bulk density is determined by EDANA recommended test method No. WSP 250.3 (11) "Gravimetric Determination of Density".

Extractables

The content of extractables of the water-absorbing polymer particles is determined by EDANA recommended test method No. WSP 270.3 (11) "Extractable". The extraction time is 16 hours.

Free Swell Rate

To determine the free swell rate (FSR), 1.00 g (=W1) of the water-absorbing polymer particles is weighed into a 25 ml beaker and distributed homogeneously over its base. Then 20 ml of a 0.9% by weight sodium chloride solution are metered into a second beaker by means of a dispenser and the contents of this beaker are added rapidly to the first and a stopwatch is started. As soon as the last drop of salt solution has been absorbed, which is recognized by the disappearance of the reflection on the liquid surface, the stopwatch is stopped. The exact amount of liquid which has been poured out of the second beaker and absorbed by the polymer in the first beaker is determined accurately by reweighing the second beaker (=W2). The time interval required for the absorption, which has been measured with the stopwatch, is designated as t. The disappearance of the last liquid droplet on the surface is determined as the time t.

The free swell rate (FSR) is calculated therefrom as follows:

$$FSR[g/g\ s]=W2/(W1\times t)$$

If the moisture content of the water-absorbing polymer particles, however, is more than 3% by weight, the weight W1 should be corrected to take account of this moisture content.

Vortex Test 50.0 ml±1.0 ml of a 0.9% by weight aqueous sodium chloride solution are introduced into a 100 ml beaker which comprises a magnetic stirrer bar of size 30 mm×6 mm. A magnetic stirrer is used to stir the sodium chloride solution at 600 rpm. Then 2.000 g±0.010 g of water-absorbing polymer particles are added as rapidly as possible, and the time taken for the stirrer vortex to disappear as a result of the absorption of the sodium chloride solution by the water-absorbing polymer particles is measured. When measuring this time, the entire contents of the beaker may still be rotating as a homogeneous gel mass, but the surface of the gelated sodium chloride solution must no longer exhibit any individual turbulences. The time taken is reported as the vortex.

EXAMPLES

Production of the Base Polymer:

Example 1

A 2 L flange vessel equipped with impeller stirrer and reflux condenser was initially charged with 340.00 g of heptane and 0.92 g of sucrose stearate (Ryoto® Sugar Ester S-370, Mitsubishi Chemical Europe GmbH, Dusseldorf, Germany), and heated to 70° C. until the sucrose stearate had dissolved fully.

A monomer solution (first metered addition), prepared from 73.40 g (1.019 mol) of acrylic acid, 61.20 g (0.765 mol) of 50% by weight aqueous sodium hydroxide solution, 109.5 g of water and 0.11 g (0.407 mmol) of potassium peroxodisulfate, was then introduced into a feed vessel and purged with air. Immediately prior to the dropwise addition of the monomer solution, at a stirrer speed of 300 rpm, the solution was inertized by means of introduction of nitrogen and an oil bath temperature of 55° C. was established.

After feeding had ended, the mixture was stirred at 70° C. for a further hour, then the reaction solution was cooled to about 25° C. and an ice-cooled monomer solution (second metered addition), prepared from 95.90 g (1.331 mol) of acrylic acid, 79.30 g (0.991 mol) of 50% by weight aqueous sodium hydroxide solution, 143.10 g of water and 0.14 g (0.518 mmol) of potassium peroxodisulfate, was introduced into a feed vessel and purged with air. Immediately prior to the dropwise addition of the monomer solution, at a stirrer speed of 300 rpm, the solution was inertized by means of introduction of nitrogen. The monomer solution was added dropwise within 15 minutes.

After the feeding had ended, an oil bath temperature of 70° C. was established. 120 minutes after commencement of heating, the reflux condenser was exchanged for a water separator and water was separated out.

The suspension present was cooled to 60° C. and the resultant polymer particles were filtered off with suction using a Büchner funnel with a paper filter. The further drying was effected at 45° C. in an air circulation drying cabinet and optionally in a vacuum drying cabinet at 800 mbar down to a residual moisture content of less than 15% by weight.

The properties of the resulting polymer particles are summarized in table 2.

Examples 2 and 3

The base polymer was produced analogously to example 1 with the amounts stated in table 1. The properties of the resulting polymer particles are summarized in table 2.

Example 4

The base polymer was produced analogously to example 1 with the amounts stated in table 1, and the first monomer solution (first metered addition) additionally comprised 3.0 g of 2-propanol (isopropanol).

The properties of the resulting polymer particles are summarized in table 2.

Example 5

A 2 L flange vessel equipped with impeller stirrer and reflux condenser was initially charged with 896.00 g of cyclohexane, 2.00 g of Span® 20 (sorbitan monolaurate), 3.20 g of Tixogel® VZ (organophilic bentonite) and 20.0 g of a 0.015% aqueous ascorbic acid solution, and heated to internal temperature 75° C. while stirring and with introduction of nitrogen.

A monomer solution, prepared from 150.00 g (2.082 mol) of acrylic acid, 125.10 g (1.613 mol) of 50% by weight aqueous sodium hydroxide solution, 138 g of water, 0.0375 g (0.243 mmol) of N,N'-methylenebisacrylamide (MBA) and 0.5 g (1.850 mmol) of potassium peroxodisulfate, was then introduced into a feed vessel and purged with air. Immediately prior to the dropwise addition of the monomer solution, at a stirrer speed of 300 rpm, the solution was inertized by means of introduction of nitrogen. Over the entire period over which the monomers were metered in, the reflux conditions were maintained. The monomer solution was added dropwise within 60 minutes.

The end of feeding was followed by a further reaction time of 60 minutes. Subsequently, the reflux condenser was exchanged for a water separator and water was separated out.

The suspension present was cooled to 60° C. and the resultant polymer particles were filtered off with suction using a Büchner funnel with a paper filter. The further drying was effected at 45° C. in an air circulation drying cabinet and optionally in a vacuum drying cabinet at 800 mbar down to a residual moisture content of less than 15% by weight.

The properties of the resulting polymer particles are summarized in table 2.

Example 6

A 2 L flange vessel equipped with impeller stirrer and reflux condenser was initially charged with 896.00 g of cyclohexane, 2.00 g of Span® 20 (sorbitan monolaurate), 3.20 g of Tixogel® VZ (organophilic bentonite) and 20.0 g of a 0.015% aqueous ascorbic acid solution, and heated to internal temperature 75° C. while stirring and with introduction of nitrogen.

A monomer solution, prepared from 150.00 g (2.082 mol) of acrylic acid, 118.0 g (1.475 mol) of 50% by weight aqueous sodium hydroxide solution, 136.8 g of water, 0.075 g (0.194 mmol) of the triacrylate of 3-tuply ethoxylated glycerol (Gly-(EO-AA)$_3$) and 0.5 g (1.850 mmol) of potassium peroxodisulfate, was then introduced into a feed vessel and purged with air. Immediately prior to the dropwise addition of the monomer solution, at a stirrer speed of 300 rpm, the solution was inertized by means of introduction of nitrogen. Over the entire period over which the monomers were metered in, the reflux conditions were maintained. The monomer solution was added dropwise within 60 minutes.

The end of feeding was followed by a further reaction time of 60 minutes. Subsequently, the reflux condenser was exchanged for a water separator and water was separated out.

The suspension present was cooled to 60° C. and the resultant polymer particles were filtered off with suction using a Büchner funnel with a paper filter. The further drying was effected at 45° C. in an air circulation drying cabinet and optionally in a vacuum drying cabinet at 800 mbar down to a residual moisture content of less than 15% by weight.

The properties of the resulting polymer particles are summarized in table 2.

TABLE 1

Amounts of crosslinker b) used

| Ex. | Step/feed | Crosslinker b) | g | mmol | ppm boaa | mmol % boaa |
|---|---|---|---|---|---|---|
| 1 | 1 | MBA | 0 | 0 | 0 | 0 |
|   | 2 | MBA | 0 | 0 | 0 | 0 |
| 2 | 1 | MBA | 0.009 | 0.06 | 125 | 6 |
|   | 2 | MBA | 0.012 | 0.08 | 125 | 6 |
| 3 | 1 | MBA | 0.018 | 0.12 | 250 | 12 |
|   | 2 | MBA | 0.023 | 0.15 | 250 | 12 |
| 4 | 1 | MBA*) | 0.018 | 0.12 | 250 | 12 |
|   | 2 | MBA*) | 0.023 | 0.15 | 250 | 12 |
| 5 | — | MBA**) | 0.0375 | 0.24 | 250 | 12 |
| 6 | — | Gly-(EO-AA)$_3$**) | 0.075 | 0.19 | 500 | 9 |

*)isopropanol as additional chain transfer reagent
**)one-stage metering
boaa: based on (unneutralized) acrylic acid
MBA: methylenebisacrylamide
Gly-(EO-AA)$_3$ triacrylate of 3-tuply ethoxylated glycerol

TABLE 2

Properties of the water-absorbing polymer particles (base polymer)

| Ex. | CRC g/g | AUNL g/g | AUL g/g | AUHL g/g | Bulk density g/100 ml | Moisture content % | Extractables % |
|---|---|---|---|---|---|---|---|
| 1 | 55.0 | 44.3 | 7.2 | 6.6 | 89 | 2.2 | 34 |
| 2 | 46.1 | 54.1 | 7.3 | 6.7 | 78 | 4.5 | 21 |
| 3 | 42.8 | 52.0 | 7.4 | 6.5 | 79 | 4.4 | 21 |
| 4 | 48.4 | 54.1 | 7.8 | 7.2 | 83 | 4.0 | 20 |
| 5 | 40.7 | 39.9 | 7.5 | 6.6 | 70 | 3.5 | 26 |
| 6 | 64.0 | 9.7 | 6.9 | 6.1 | 91 | 2.0 | 29 |

Thermal Surface Postcrosslinking:

Examples 1-1 and 1-2

20 g of base polymer from example 1 were introduced into a mixer of the Waring® 32BL80 (8011) blender type. Subsequently, the mixer was switched on at level 1. Immediately thereafter, 1.5 g of an aqueous solution consisting of 0.5 g of ethylene carbonate and 1.0 g of water, according to table 3, were introduced into a pipette and metered into the mixer within 2 seconds. After 3 seconds, the mixer was switched off and the resultant polymer particles were distributed homogeneously in a glass dish having a diameter of 20 cm. For thermal surface postcrosslinking, the glass dish filled with the polymer particles was heated in an air circulation drying cabinet at 160° C. for 60 or 120 minutes. The polymer particles were transferred to a cold glass dish. Finally, the coarser particles were removed with a sieve having a mesh size of 850 μm.

The properties of the polymer particles are summarized in table 4.

Examples 2-1 and 2-2

The thermal surface postcrosslinking was effected analogously to example 1-1 and 1-2, except using the base polymer from example 2. The temperature in the air circulation drying cabinet was 160° C. The heat treatment time was 60 or 120 minutes. The conditions are summarized in table 3.

The properties of the polymer particles are summarized in table 4.

Examples 3-1 and 3-2

The thermal surface postcrosslinking was effected analogously to example 1-1 and 1-2, except using the base polymer from example 3. The temperature in the air circulation drying cabinet was 160° C. The heat treatment time was 60 or 120 minutes. The conditions are summarized in table 3.

The properties of the polymer particles are summarized in table 4.

Examples 3-3 and 3-4

The thermal surface postcrosslinking was effected analogously to example 1-1, except using the base polymer from example 3 and using N,N,N',N'-tetrakis(2-hydroxyethyl)ethylenediamine (Primid® XL 552) as surface postcrosslinker. The temperature in the air circulation drying cabinet was 160° C. The heat treatment time was 60 minutes. The conditions are summarized in table 3.

The properties of the polymer particles are summarized in table 4.

Examples 3-5 and 3-6

The thermal surface postcrosslinking was effected analogously to example 1-1, except using the base polymer from example 3. The temperature in the air circulation drying cabinet was 90° C. or 200° C. The heat treatment time was 60 minutes. The conditions are summarized in table 3.

The properties of the polymer particles are summarized in table 4.

Examples 4-1 and 4-2

The thermal surface postcrosslinking was effected analogously to example 1-1 and 1-2, except using the base polymer from example 4. The temperature in the air circulation drying cabinet was 160° C. The heat treatment time was 60 or 120 minutes. The conditions are summarized in table 3.

The properties of the polymer particles are summarized in table 4.

Examples 5-1 and 5-2

The thermal surface postcrosslinking was effected analogously to example 1-1 and 1-2, except using the base polymer from example 5. The temperature in the air circulation drying cabinet was 160° C. The heat treatment time was 60 or 120 minutes. The conditions are summarized in table 3.

The properties of the polymer particles are summarized in table 4.

Examples 6-1 and 6-2

The thermal surface postcrosslinking was effected analogously to example 1-1 and 1-2, except using the base polymer from example 6. The temperature in the air circulation drying cabinet was 160° C. The heat treatment time was 60 or 120 minutes. The conditions are summarized in table 3.

The properties of the polymer particles are summarized in table 4.

Example 7

Example 1 from U.S. Pat. No. 8,003,210 was reworked.
The properties of the polymer particles are summarized in table 4.

TABLE 3

Thermal surface postcrosslinking in Waring ® blender - conditions

| Ex. Crosslinker b) | Temperature ° C. | Time min | Ethylene carbonate % by wt. bop | Ethylene carbonate mmol per 20 g of polymer | Water % by wt. bop | Primid ® XL 552 % by wt. bop | Primid ® XL 552 mmol per 20 g of polymer |
|---|---|---|---|---|---|---|---|
| 1  0 ppm MBA | — | — | — | — | — | — | — |
| 1-1 | 160 | 60 | 2.5 | 5.68 | 5 | — | — |
| 1-2 | 160 | 120 | 2.5 | 5.68 | 5 | — | — |
| 2  125 ppm MBA | — | — | — | — | — | — | — |
| 2-1 | 160 | 60 | 2.5 | 5.68 | 5 | — | — |
| 2-2 | 160 | 120 | 2.5 | 5.68 | 5 | — | — |
| 3  250 ppm MBA | — | — | — | — | — | — | — |
| 3-1 | 160 | 60 | 2.5 | 5.68 | 5 | — | — |
| 3-2 | 160 | 120 | 2.5 | 5.68 | 5 | — | — |
| 3-3 | 160 | 60 | — | — | 5 | 4.55 | 2.84 |
| 3-4 | 160 | 60 | — | — | 5 | 9.05 | 5.68 |
| 3-5 | 90 | 60 | 2.5 | 5.68 | 5 | — | — |
| 3-6 | 200 | 60 | 2.5 | 5.68 | 5 | — | — |
| 4  250 ppm MBA*) | — | — | — | — | — | — | — |
| 4-1 | 160 | 60 | 2.5 | 5.68 | 5 | — | — |
| 4-2 | 160 | 120 | 2.5 | 5.68 | 5 | — | — |
| 5  250 ppm MBA**) | — | — | — | — | — | — | — |
| 5-1 | 160 | 60 | 2.5 | 5.68 | 5 | — | — |
| 5-2 | 160 | 120 | 2.5 | 5.68 | 5 | — | — |
| 6  500 ppm Gly-(EO-AA)$_3$**) | — | — | — | — | — | — | — |
| 6-1 | 160 | 60 | 2.5 | 5.68 | 5 | — | — |
| 6-2 | 160 | 120 | 2.5 | 5.68 | 5 | — | — | bop: based on (base) polymer
*)isopropanol as additional chain transfer reagent
**)one-stage agglomeration

TABLE 4

Thermal surface postcrosslinking in Waring ® blender - properties of the polymer particles

| Ex. | CRC g/g | AUNL g/g | AUL g/g | AUHL g/g | Moisture content % by wt. | Extractables % by wt. | Vortex s | FSR g/g s | CRC + AUL g/g | CRC + AUHL g/g |
|---|---|---|---|---|---|---|---|---|---|---|
| 1 | 55.0 | 44.3 | 7.2 | 6.6 | 2.2 | 34 | 200 | 0.06 | 62.2 | 61.6 |
| 1-1 | 46.0 | 59.0 | 26.0 | 9.3 | 1.2 | 5 | 194 | 0.08 | 72.0 | 55.3 |
| 1-2 | 43.8 | 55.5 | 34.0 | 19.7 | 1.1 | 13 | 192 | 0.12 | 77.8 | 63.5 |
| 2 | 46.1 | 54.1 | 7.32 | 6.7 | 4.5 | 21 | 96 | 0.27 | 53.4 | 52.79 |
| 2-1 | 37.5 | 63.8 | 32.9 | 10.7 | 0.6 | 6 | 100 | 0.19 | 70.4 | 48.2 |
| 2-2 | 37.5 | 60.4 | 38.7 | 24.3 | 0.8 | 4 | 95 | 0.15 | 76.2 | 61.8 |
| 3 | 42.8 | 52.0 | 7.4 | 6.5 | 4.4 | 21 | 70 | 0.28 | 50.2 | 49.3 |
| 3-1 | 38.8 | 61.1 | 36.4 | 17.8 | 1.2 | 17 | 85 | 0.12 | 75.2 | 56.6 |
| 3-2 | 34.0 | 61.9 | 32.9 | 18.1 | 1.1 | 8 | 91 | 0.15 | 66.9 | 52.1 |
| 3-3 | 30.4 | 50.0 | 22.5 | 15.1 | 0.8 | 18 | 50 | 0.34 | 52.9 | 45.5 |
| 3-4 | 29.1 | 42.6 | 22.4 | 14.9 | 1.2 | 21 | 75 | 0.30 | 51.5 | 43.9 |
| 3-5*) | 41.9 | 52.6 | 7.6 | 7.1 | 2.9 | 22 | 71 | 0.26 | 49.5 | 49.0 |
| 3-6*) | 29.0 | 49.2 | 26.2 | 14.2 | 1.3 | 21 | 76 | 0.33 | 55.2 | 43.2 |
| 4 | 48.4 | 54.1 | 7.8 | 7.2 | 4.0 | 20 | 130 | 0.13 | 56.2 | 55.6 |
| 4-1 | 45.0 | 62.3 | 37.5 | 14.4 | 1.7 | 3 | 120 | 0.07 | 82.5 | 59.4 |
| 4-2 | 42.8 | 60.2 | 39.3 | 26.2 | 1.2 | 3 | 127 | 0.10 | 82.1 | 69.0 |
| 5 | 40.7 | 39.3 | 7.5 | 6.6 | 3.5 | 26 | 60 | 0.09 | 48.2 | 47.3 |
| 5-1 | 40.1 | 53.7 | 18.8 | 7.2 | 2.4 | 16.1 | 50 | 0.14 | 58.9 | 47.3 |
| 5-2 | 37.8 | 55.3 | 33.0 | 16.3 | 0.9 | 11.2 | 49 | 0.18 | 70.8 | 54.1 |
| 6 | 64.0 | 9.7 | 6.9 | 6.1 | 2 | 29 | 92 | 0.18 | 70.9 | 70.1 |
| 6-1 | 45.2 | 53.0 | 26.9 | 12.1 | 1.1 | 18.3 | 90 | 0.13 | 72.1 | 57.3 |
| 6-2 | 40.5 | 56.6 | 30.3 | 16.3 | 0.9 | 12.0 | 90 | 0.11 | 70.8 | 56.8 |
| 7*) | 44.3 | 63.9 | 12.1 | 7.1 | 4.0 | 22 | 62 | 0.33 | 56.4 | 51.4 |

*)comparative example

The invention claimed is:

1. A process for producing water-absorbing polymer particles by polymerizing a monomer solution comprising
   a) at least one ethylenically unsaturated monomer which bears an acid group and optionally is at least partly neutralized,
   b) optionally one or more crosslinker,
   c) at least one initiator,
   d) optionally one or more ethylenically unsaturated monomer copolymerizable with the monomer mentioned under a), and
   e) optionally one or more water-soluble polymer,
   the monomer solution suspended in a hydrophobic organic solvent during the polymerization and agglomerating in the hydrophobic organic solvent during or after the polymerization, and thermally surface postcrosslinking the resultant agglomerated polymer particles by means of an organic surface postcrosslinker, wherein the amount of crosslinker b) is selected such that the agglomerated polymer particles before the surface postcrosslinking have a centrifuge retention capacity of at least 37 g/g and the thermal surface postcrosslinking is conducted at 100 to 190° C.,
   wherein the water-absorbing polymer particles have a centrifuge retention capacity of at least 37 g/g, an absorption under a pressure of 21.0 g/cm² of at least 30 g/g, an absorption under a pressure of 49.2 g/cm² of at least 14 g/g, a sum total of centrifuge retention capacity and absorption under a pressure of 21.0 g/cm² of at least 69 g/g, a sum total of centrifuge retention capacity and absorption under a pressure of 49.2 g/cm² of at least 54 g/g, and less than 20% by weight of extractables.

2. The process according to claim 1, wherein agglomeration is effected in the hydrophobic organic solvent after the polymerization.

3. The process according to claim 1, wherein the polymerization is conducted in the presence of a chain transfer reagent.

4. The process according to claim 1, wherein the amount of crosslinker b) is selected such that the polymer particles before the surface postcrosslinking have a centrifuge retention capacity of at least 40 g/g.

5. The process according to claim 1, wherein the thermal surface postcrosslinking is conducted at 120 to 170° C.

6. The process according to claim 1, wherein the organic surface postcrosslinker is selected from the group consisting of alkylene carbonates, 2-oxazolidinones, bis- and poly-2-oxazolidinones, 2-oxotetrahydro-1,3-oxazines, N-acyl-2-oxazolidinones, cyclic ureas, bicyclic amido acetals, oxetanes, and morpholine-2,3-diones.

7. The process according to claim 1, wherein from 1 to 5% by weight of organic surface postcrosslinker is used, based on the resultant polymer particles.

8. The process according to claim 1, wherein at least one dispersing aid is used in the polymerization.

9. The process according to claim 1, wherein the resultant polymer particles are at least partly dewatered azeotropically after the polymerization.

10. The process according to claim 9, wherein the resultant polymer particles are filtered and dried after the azeotropic dewatering.

11. The process according to claim 1, wherein the thermal surface postcrosslinking is conducted in a mixer with moving mixing tools.

* * * * *